US00PP15710P3

(12) United States Plant Patent
Redman

(10) Patent No.: US PP15,710 P3
(45) Date of Patent: Apr. 5, 2005

(54) ***CHRYSANTHEMUM* PLANT NAMED 'VAMP TIME BRONZE'**

(50) Latin Name: *Chrysanthemum morifolium*
Varietal Denomination: Vamp Time Bronze

(75) Inventor: Ruth Redman, Bognor Regis (GB)

(73) Assignee: Cleangro LTD (GB)

( * ) Notice: Subject to any disclaimer, the term of this patent is extended or adjusted under 35 U.S.C. 154(b) by 87 days.

(21) Appl. No.: 10/365,160

(22) Filed: Feb. 11, 2003

(65) Prior Publication Data

US 2004/0158901 P1 Aug. 12, 2004

(30) Foreign Application Priority Data

Apr. 23, 2001 (QZ) ..... PBR 20019999

(51) Int. Cl.[7] ..... A01H 5/00
(52) U.S. Cl. ..... Plt./290
(58) Field of Search ..... Plt./290

(56) References Cited

PUBLICATIONS

U.S. Plant Patent Application Publication No. US 2003/0056289 P1, pub. date Mar. 20, 2003, Appl. No. 09/957,486 filed Sep. 19, 2001, for variety "Drive Time," Inventor Mark Roland Broeder.

2001 Floor Catalog listing variety 'Vamp Time,' See, e.g., p. 4.

2002 Floor Catalog listing variety 'Vamp Time,' See, e.g., p. 4.

*Primary Examiner*—Ann Marie Grunberg
(74) *Attorney, Agent, or Firm*—Howrey Simon Arnold & White, LLP

(57) ABSTRACT

A new variety of *Chrysanthemum* plant named 'Vamp Time Bronze,' having a good uniform canopy of bronze decorative flowers. The new variety has a medium vigor, free branching, with a uniform spreading habit and good foliage presentation.

1 Drawing Sheet

Latin name of the genus and species: Botanical classification: *Chrysanthemum morifolium.*

Variety denomination: The new *Chrysanthemum* variety denomination is 'Vamp Time Bronze.'

BACKGROUND OF THE INVENTION

The present invention comprises a new and distinct cultivar of *Chrysanthemum* botanically known as *Chrysanthemum morifolium,* and referred to by the cultivar name 'Vamp Time Bronze,' 'Vamp Time Bronze.' identified as 20544-2, originated from a whole plant mutation grown in a controlled planting of the unpatented variety 'Vamp Time,' in Chichester, West Sussex, United Kingdom. The new variety 'Vamp Time Bronze' has been asexually reproduced by vegetative cuttings in Chichester, West Sussex, United Kingdom and the distinguishing characteristics are retained through successive generations of asexual reproduction.

BRIEF SUMMARY OF THE INVENTION

'Vamp Time Bronze' is a pot type of *Chrysanthemum* plant variety having bronze decorative flowers with a domed capitulum form.

Comparison with Parent

Plants of the new *Chrysanthemum* variety 'Vamp Time Bronze' are similar to the parent cultivar 'Vamp Time' in plant habitat and growth rate. In side-by-side comparisons in Chichester, West Sussex, United Kingdom, under commercial practice, plants of the new *Chrysanthemum* variety 'Vamp Time Bronze' compared to plants of the parent cultivar 'Vamp Time' in the following characteristics.

1. The new variety 'Vamp Time Bronze' produces orange bronze decorative flowers whereas the parent cultivar 'Vamp Time' produces light pink flowers.
2. Plants of the new variety 'Vamp Time Bronze' have similar inflorescence to plants of the parent cultivar 'Vamp Time.'

Comparison with Other Varieties

Plants of the new *Chrysanthemum* variety 'Vamp Time Bronze' are similar to the cultivar 'Drive Time' (U.S. Plant patent application Ser. No. 09/957,486), in plant habitat and growth rate. However, in side-by-side comparisons in Chichester, West Sussex, United Kingdom, under commercial practice, plants of the new *Chrysanthemum* variety 'Vamp Time Bronze' differed from plants of the cultivar 'Drive Time' in the following characteristics.

1. The new variety 'Vamp Time Bronze' produces orange bronze decorative flowers whereas the 'Drive Time' produces bronze decorative flowers.
2. Plants of the new variety 'Vamp Time Bronze' have larger and taller inflorescence than plants of the 'Drive Time.'

BRIEF DESCRIPTION OF ILLUSTRATION

Typical specimens of the plant and flowers for the new *Chrysanthemum* variety 'Vamp Time Bronze' are shown in the accompanying digital photograph. The colors shown are as true as possible within the usual limits of this kind of illustration.

FIG. 1 is a whole plant view of the new variety 'Vamp Time Bronze' grown in a pot. The plant shown in the illustration is 54 day from the commencement of Short Days.

DETAILED BOTANICAL DESCRIPTION

The following description of the new *Chrysanthemum* variety 'Vamp Time Bronze' is of plants grown in a greenhouse in Chichester, West Sussex, United Kingdom in the month of May. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 19° C. at night and about 17° C. to 24° C. during the day under light conditions of about 5000 to 6000 foot candles. The plants respond well to the use of growth retardant, such as B9 treatment at about 2 g per liter. To produce a commercial product the plants may be pinched once with the center bud removed. The typical container size for commercial growth is 1 liter. It has been observed that the shelf life of the new variety is about 28 days with a response time of about 7.5 weeks. The new variety is suitable for growth in a temperature range of 15° C. to 25° C.

The new variety may be produced as a spray. The following description is with respect to a plant produced as pot *Chrysanthemum.* In the description of this new *Chrysanthemum* variety, color values have been taken from The Royal Horticultural Society Colour Chart (R.H.S.C.C.).

Plant

Plant type: Pot.
Habit: Upright and free branching.
Height: 20 cm.
Width: 32 cm.
Branching characteristics: Upright and free branching.
Length of lateral branches: 12 cm.
Number of breaks from pinch: 4.
Stem color: 138B.
Response time: 52 days.
Vigor: Medium.
Shelf life: 28 days.
Disease/pest (susceptibility/resistance observed): None observed to date.
Growth retardant type and treatment: 3 applications of 2.5 gm/liter B9 @ 2, 21 and 28 days after sticking unrooted cuttings.

The plants were grown for 2 weeks in Long Day conditions (20 hours of light) and then transferred to Short Day conditions (13 hours of dark).

Propagation:
- *Type.*—vegetative propagation via stem cuttings.
- *Time to rooting.*—14 days with soil temperatures of 18° C.
- *Rooting habit.*—After 7 days the first roots emerge and form root primodia. In 14 Long Days a complete root system is developed.

Foliage

Number of leaves per lateral branch: 9.
Compound or single: Single.
Arrangement of leaves: Alternate.
- *Shape of leaf.*—Typically 5 lobed.
- *Size of leaf*—Width (cm): 4.5 Length (cm): 7.
- *Leaf apex.*—Acute.
- *Base.*—Cordate.
- *Attachment*—Petioled.
- *Aspect.*—Slightly undulating.
- *Margin.*—Lobed.
- *Surface characteristics.*—Top: slightly pubescent. Bottom: pubescent.

Petiole: Color: 138A. Length: 1.3 cm.
Venation: Net prominent mid vein at underside. Color: Upper side: near 147C. Under side: 147C.
Color: Mature Leaf, upper side: near 137A; under side: near 137C. Young Leaf, upper side: near 147A; under side: near 137C.

Flower

Flower appearance: Matte.
Flower type: Decorative.
Flower form: Domed.
Flower shape: Round.
Flowering habit: Domed capitulam.
Number of blossoms per branch: 4.
Inflorescence form: Cyme.
- *Depth of fully expanded blossoms.*—1.5 cm.
- *Diameter of fully expanded blossoms.*—9 cm.

Phyllaries:
- *Number.*—13.
- *Color.*—138A.
- *Length.*—0.7 cm.
- *Width.*—4 cm.
- *Texture/Appearance.*—pubescent.

Peduncle: Peduncle length is shortest at the terminal flower and progressively longer moving down the stem.
- *Length*—8.5 cm (average).
- *Color.*—Near 138B.
- *Surface.*—Slightly pubescent.
- *Habit.*—Slightly undulating.
- *Strength.*—Medium.

Pedicle: Length: terminal: 3 cm; lateral: 3.5 cm.
- *Color.*—Near 138B.
- *Surface.*—Slightly pubescent.
- *Habit.*—Slightly undulating.
- *Strength.*—Medium.

Ray florets:
- *Form/shape.*—Straight.
- *Texture/appearance.*—Matte.
- *Number per flower.*—95.
- *Length.*—4 cm; Width: 1.3 cm.
- *Apex.*—Dentate.
- *Base.*—Tapered.
- *Margin.*—Entire.

Disc florets per individual flower:
- *Form/shape.*—Cylindric.
- *Texture/appearance.*—Shiny.
- *Number per flower.*—14.
- *Length.*—0.5 cm; Width: 0.1 cm.
- *Diameter of disc.*—0.3 cm.

Fragrance: None.
Flower bud (at onset of color):
- *Length.*—1.8 cm.
- *Diameter.*—1.5 cm.
- *Form/shape.*—Spherical.

General flower color:
1. *Ray florets, upper side.*—22A. Immature: near 26B. Mature: near 22C. Older/Fading: near 20A.
2. *Ray florets, under side.*—26C. Immature: near 26B. Mature: near 26C. Older/Fading: near 26C.

*3. Disc florets.*—Immature: near 145B. Mature: near 145B. Older/Fading: near 145C.

*4. Bud.*—22A.

Flower progression with age: Flower form does not change but there is a slight color fading with age.

Reproductive Organs

Gynoecium present on Ray and Disc florets.

Ray florets:

*Pistil number.*—95.

*Stigma color.*—Near 3A.

*Stigma shape.*—Forked.

*Style color.*—Near 154B.

*Style length.*—0.4 cm.

Disc florets per individual flower:

*Pistil number.*—14.

*Stigma color.*—Near 3A.

*Stigma shape.*—Forked.

*Style color.*—Nnear 154B.

*Style length.*—0.4 cm.

Androecium not observed.

Fruit and seeds: None observed.

What is claimed is:

1. A new and distinct variety of *Chrysanthemum* plant, substantially as described and illustrated herein.

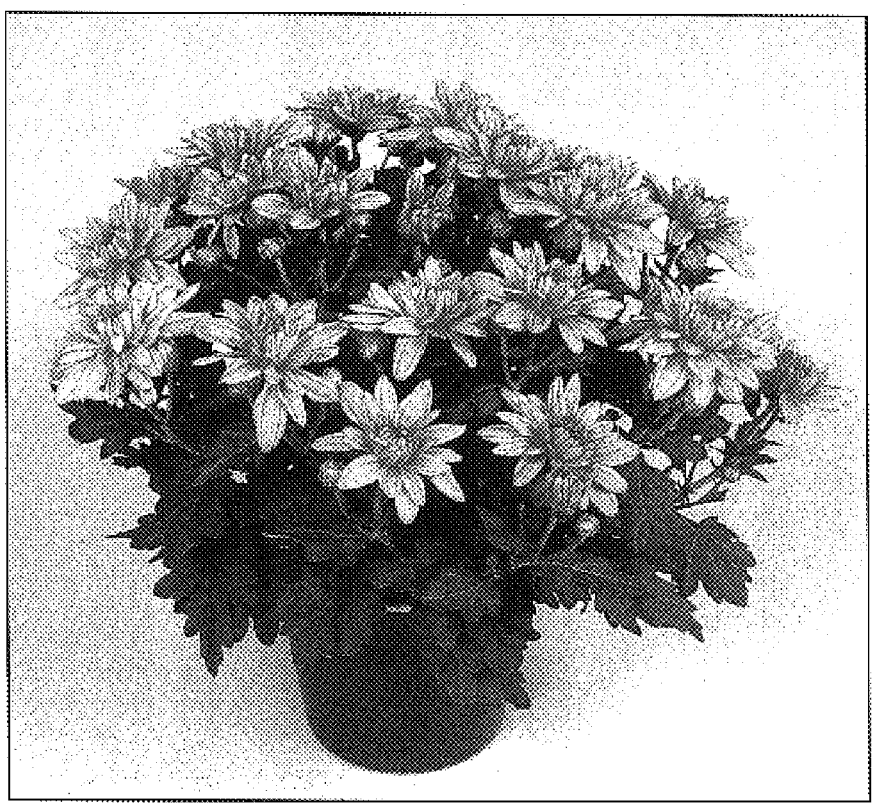

* * * * *